(12) United States Patent
Krimmer et al.

(10) Patent No.: US 10,736,542 B2
(45) Date of Patent: Aug. 11, 2020

(54) INSOLE OR SHOE SOLE

(71) Applicant: stAPPtronics GmH, Sulz (AT)

(72) Inventors: Peter Krimmer, Vienna (AT); Philip Olbrich, Vienna (AT); Thomas Frois, Sulz (AT)

(73) Assignee: stAPPtronics GmH, Sulz (AT)

( * ) Notice: Subject to any disclaimer, the term of this patent is extended or adjusted under 35 U.S.C. 154(b) by 304 days.

(21) Appl. No.: 15/716,958

(22) Filed: Sep. 27, 2017

(65) Prior Publication Data

US 2018/0085030 A1  Mar. 29, 2018

(30) Foreign Application Priority Data

Sep. 27, 2016  (AT) ..................... 443/2016

(51) Int. Cl.
*A61B 5/103* (2006.01)
*A43B 13/12* (2006.01)
(Continued)

(52) U.S. Cl.
CPC .......... *A61B 5/1036* (2013.01); *A43B 3/0005* (2013.01); *A43B 3/0031* (2013.01);
(Continued)

(58) Field of Classification Search
CPC ... A61B 5/1036; A61B 5/6829; A43B 17/006; A43B 13/12; A43B 3/0031; A43B 13/37; A43B 3/0005; A43B 13/14
See application file for complete search history.

(56) References Cited

U.S. PATENT DOCUMENTS 6,195,921 B1  3/2001  Truong
2005/0217142 A1  10/2005  Ellis, III
(Continued)

FOREIGN PATENT DOCUMENTS

CN  103169598  6/2013
CN  104172641  12/2014
(Continued)

OTHER PUBLICATIONS https://www.kickstarter.com/projects/smartmove/smartmove-accuracy-you-can-trust-change-made-easy?ref=nav_search&result=project&term=smartmove, May 23, 2014.
(Continued)

*Primary Examiner* — Christian Jang
(74) *Attorney, Agent, or Firm* — Volpe and Koenig, P.C.

(57) ABSTRACT

Insole or shoe sole, which has a sensor device (10) having a plurality of sensor fields (1-9) for pressure detection and an electronic unit (15) that is electrically connected to the sensor fields (1-9) and has electronic components (17), wherein the sensor device (10) is formed in the manner of a sandwich with a middle layer (12) made of a piezoresistive material, a top layer (13) arranged above the middle layer (12) and a bottom layer (11) arranged underneath the middle layer (12). The top and bottom layer (13, 11) each include an electrically conductive material (14) in the region (1a-9a; 1b-9b) of a respective sensor field (1-9). The top and bottom layer (13, 11) each have a protruding flexible tab (23, 22) having conductor tracks (24-26) for electrically connecting the sensor fields (1-9) to the electronic unit (15). The electronic unit (15) has contact regions (29), against which the tabs (23, 22) bear by way of their conductor tracks (24-26).

11 Claims, 5 Drawing Sheets

(51) Int. Cl.
*A43B 3/00* (2006.01)
*A43B 17/00* (2006.01)
*A43B 13/37* (2006.01)
*A61B 5/00* (2006.01)
*A43B 13/14* (2006.01)

(52) U.S. Cl.
CPC .............. *A43B 13/12* (2013.01); *A43B 13/37* (2013.01); *A43B 17/006* (2013.01); *A61B 5/6829* (2013.01); *A43B 13/14* (2013.01)

(56) References Cited

U.S. PATENT DOCUMENTS

| | | | |
|---|---|---|---|
| 2006/0035486 | A1* | 2/2006 | Higuchi .............. H01R 12/52 439/66 |
| 2007/0112285 | A1 | 5/2007 | Dar et al. |
| 2009/0011633 | A1* | 1/2009 | Busse .............. H01R 4/2425 439/404 |
| 2010/0004566 | A1 | 1/2010 | Son et al. |
| 2010/0063778 | A1 | 3/2010 | Schrock et al. |
| 2010/0201650 | A1 | 8/2010 | Son |
| 2010/0217159 | A1 | 8/2010 | Wukasch et al. |
| 2011/0214501 | A1 | 9/2011 | Ross et al. |
| 2012/0291564 | A1 | 11/2012 | Amos et al. |
| 2013/0211775 | A1 | 8/2013 | Statham |
| 2013/0213146 | A1 | 8/2013 | Amos et al. |
| 2014/0007704 | A1 | 1/2014 | Granado et al. |
| 2014/0130381 | A1 | 5/2014 | Jung |
| 2014/0149072 | A1 | 5/2014 | Rutschmann |
| 2014/0266570 | A1 | 9/2014 | Sharma et al. |
| 2014/0276236 | A1 | 9/2014 | Swain et al. |
| 2014/0326085 | A1 | 11/2014 | Lee |
| 2015/0330855 | A1* | 11/2015 | Daniecki .............. A43B 3/0005 73/727 |
| 2015/0351484 | A1 | 12/2015 | Rubin et al. |
| 2015/0359457 | A1 | 12/2015 | Blumenthal et al. |
| 2015/0359460 | A1 | 12/2015 | Rubin et al. |
| 2016/0349076 | A1 | 12/2016 | Campos Gallo et al. |
| 2017/0188950 | A1* | 7/2017 | Gazdag .............. A61B 5/6807 |
| 2018/0249945 | A1* | 9/2018 | Najafi .............. A61B 5/1038 |

FOREIGN PATENT DOCUMENTS

| | | |
|---|---|---|
| CN | 204146420 | 2/2015 |
| CN | 204580070 | 8/2015 |
| CN | 105231577 | 1/2016 |
| CN | 105266256 | 1/2016 |
| CN | 105266257 | 1/2016 |
| CN | 105380342 | 3/2016 |
| CN | 205082778 | 3/2016 |
| CN | 205215232 | 5/2016 |
| CN | 105662418 | 6/2016 |
| CN | 105662423 | 6/2016 |
| CN | 205306138 | 6/2016 |
| CN | 205321406 | 6/2016 |
| CN | 105725982 | 7/2016 |
| CN | 205358441 | 7/2016 |
| DE | 10201134 | 7/2003 |
| DE | 102006025447 | 12/2007 |
| DE | 102010049154 | 6/2011 |
| DE | 102009060794 | 7/2011 |
| DE | 102010012037 | 9/2011 |
| DE | 102010013671 | 10/2011 |
| DE | 102011009969 | 8/2012 |
| DE | 102011012458 | 8/2012 |
| DE | 102011100933 | 11/2012 |
| DE | 102011122659 | 7/2013 |
| DE | 102012004117 | 9/2013 |
| DE | 102013202878 | 9/2014 |
| DE | 102013210213 | 12/2014 |
| DE | 102013015848 | 3/2015 |
| DE | 202015004254 | 11/2015 |
| EP | 3047794 | 7/2016 |
| EP | 3223163 | 9/2017 |
| KR | 101530225 | 6/2015 |
| KR | 20150088072 | 7/2015 |
| WO | 9718450 | 5/1997 |
| WO | 2014016260 | 1/2014 |
| WO | 2014154352 | 10/2014 |
| WO | 2016086491 | 6/2016 |
| WO | 2016092313 | 6/2016 |
| WO | 2016111425 | 7/2016 |
| WO | 2016138234 | 9/2016 |

OTHER PUBLICATIONS https://www.kickstarter.com/projects/stridalyzer/stridalyzer-smart-insoles?ref=nav_search&result=projct&term=stridalyzer, Jan. 3, 2015.

* cited by examiner

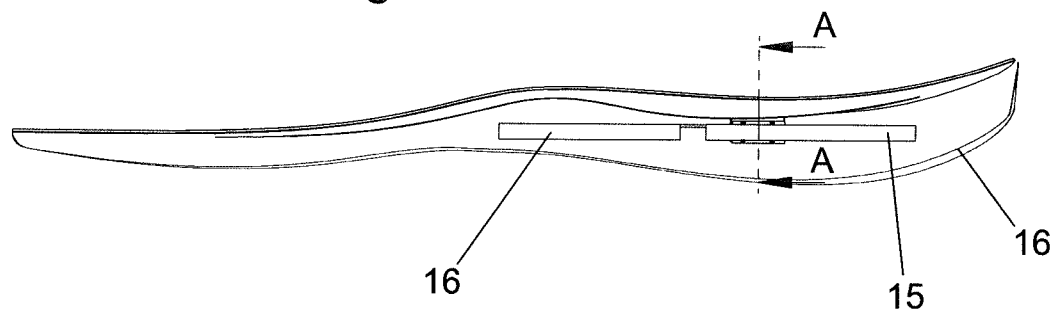
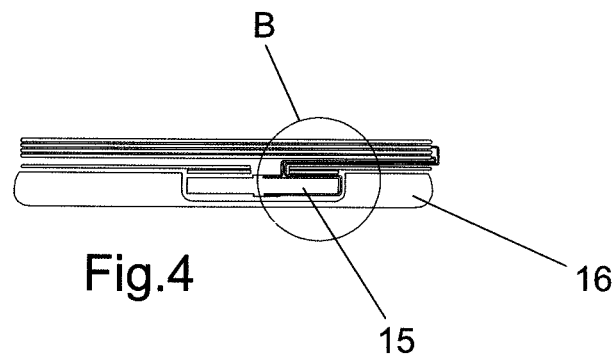
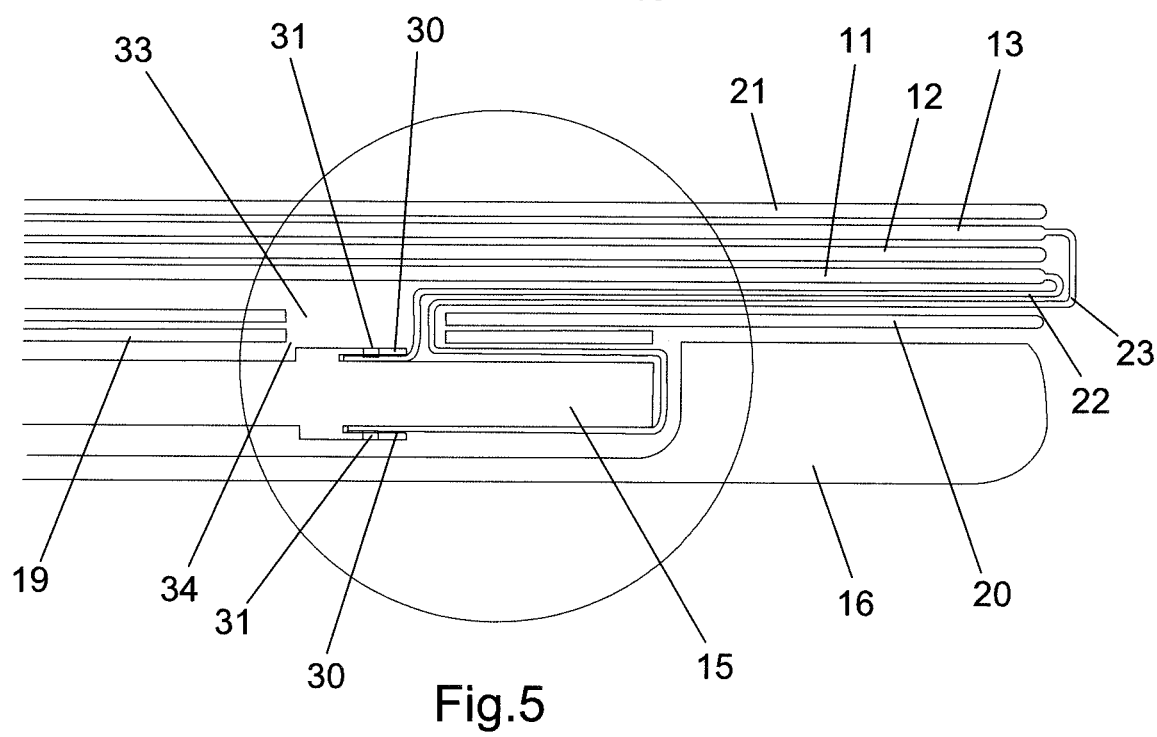

INSOLE OR SHOE SOLE

INCORPORATION BY REFERENCE

The following documents are incorporated herein by reference as if fully set forth: Austrian Patent Application No. A443/2016, filed Sep. 27, 2016.

BACKGROUND

The invention relates to an insole or shoe sole, which has a sensor device having a plurality of sensor fields for pressure detection and an electronic unit that is electrically connected to the sensor fields and has electronic components.

It is possible to use insoles or shoe soles of this kind to detect and evaluate, inter alia, movement sequences of a user, in order to determine incorrect load distribution, for example. To this end, the pressure on the individual sensor fields and the temporal pressure profile can be detected and evaluated.

DE 10 2006 025 447 A1 discloses an insole, which has a plurality of sensors. A respective sensor can comprise a piezoresistive material or else can be designed as a capacitive sensor. An electronic unit can likewise be integrated into the insole, said electronic unit being electrically connected to the sensors and evaluating the signals output by the sensors. A similar insole is disclosed in DE 10 201 134 A1.

DE 10 2012 004 117 A1 discloses a device of the type mentioned at the outset designed as an insole or shoe sole, said device having a sensor device with a plurality of sensor fields for pressure detection and an electronic unit having electronic components that are electrically connected to the sensor fields. The electronic unit is a rigid-flexible printed circuit board, which is populated with the electronic components. The sensor fields of the sensor device are designed as capacitive sensors. For this purpose, the sensor device has a first capacitor plate side, which is designed as a textile sensor layer, and a second capacitor plate side, which is formed by an electrically conductive ground layer. The two capacitor plate sides are isolated by a deformable dielectric. The textile sensor layer has a plurality of conductive regions to form the sensor fields, said conductive regions being connected to sensor connection gates by sensor supply lines, said sensor connection gates being arranged in central regions of the textile sensor layer. The sensor connection gates bear against the connection gates of the printed circuit board.

EP 3 047 794 A1 discloses a textile piezoresistive sensor for detecting heart rate and breathing, said sensor being particularly suited to being integrated into covers for beds, chairs or vehicle seats. The sensor comprises a first textile layer, onto which strips of conductive material are applied by imprinting, weaving or embroidering, a second layer designed in a similar manner and a layer made of a piezoresistive material arranged between these two layers.

SUMMARY

It is the object of the invention to provide an advantageous insole or shoe sole of the type mentioned at the outset, which is distinguished by a simple design and can be produced in a simple manner. This is achieved by an insole or shoe sole having one or more features of the invention.

In the insole or shoe sole according to the invention, the sensor device has a sandwich structure with a middle layer made of a piezoresistive material, a top layer arranged above the middle layer and a bottom layer arranged underneath the middle layer, wherein the top and bottom layer each comprise an electrically conductive material in the region of a respective sensor field. Piezoresistive sensor fields are therefore formed in this way. The top and bottom layer each have a protruding flexible tab having conductor tracks for electrically connecting the sensor fields to the electronic unit and the electronic unit has contact regions, against which the tabs bear by way of their conductor tracks.

Simple evaluation of the measurement signals is made possible by forming the shoe sole with piezoresistive sensors. Since piezoresistive sensors are formed by the sensor fields of the sensor device, which comprises the middle layer, top layer and bottom layer, in connection with the protruding flexible tabs, which the top and bottom layer comprise, a simple design as well as simple produceability is achieved. Conductor tracks, with which the tabs are provided, are borne against contact regions of the electronic unit for electrically connecting the sensor fields to the electrical components of the electronic unit.

In the state in which the electronic unit is connected, the tabs arranged on the top and bottom layer are advantageously bent over or folded over in the region in which they protrude from the respective layer. The contact regions for the conductor tracks of the bottom tab can advantageously be arranged on the top side of the electronic unit and the contact regions for the conductor tracks of the top tab can advantageously be arranged on the bottom side of the electronic unit. In one advantageous embodiment, clamping elements, for example in the form of resiliently elastic tongues, can be provided for pressing the conductor tracks onto the contact regions of the electronic unit. Instead or as an alternative, the tabs could also be adhesively bonded to the electronic unit.

In the state in which the electronic unit is connected, a respective tab can have at least one hole, through which a positioning pin protrudes to facilitate the positioning of said tab. The at least one positioning pin can in this case be arranged on the clamping element, in particular.

In one preferred embodiment of the invention, the electrically conductive material for forming a respective sensor field is formed by an electrically conductive yarn embroidered onto a base material of the top or bottom layer. In this case, it is advantageous for the conductor tracks of the tabs to be formed by an embroidered-on, electrically conductive yarn of this kind as well. The sensor supply lines, which extend the conductor tracks of the tabs and connect said conductor tracks to the sensor fields, can also be formed by an embroidered-on, electrically conductive yarn. It is particularly advantageous for all of the electrically conductive parts of the top and bottom layer to be formed by an embroidered-on, electrically conductive yarn.

In an alternative embodiment of the invention, however, it would also be conceivable and possible for the electrically conductive material in the region of a respective sensor field and/or the conductor tracks of the tabs and/or the sensor supply lines to be formed by an electrically conductive coating.

BRIEF DESCRIPTION OF THE DRAWINGS

Further advantages and details of the invention will be explained in the following text with reference to the accompanying drawing, in which:

FIG. 3 shows a side view (illustrated with the sole base part being transparent);

FIG. 4 shows a section along the line AA of FIG. 3;

FIG. 5 shows an enlarged part B of FIG. 4;

DETAILED DESCRIPTION OF THE PREFERRED EMBODIMENTS

Figure 1:
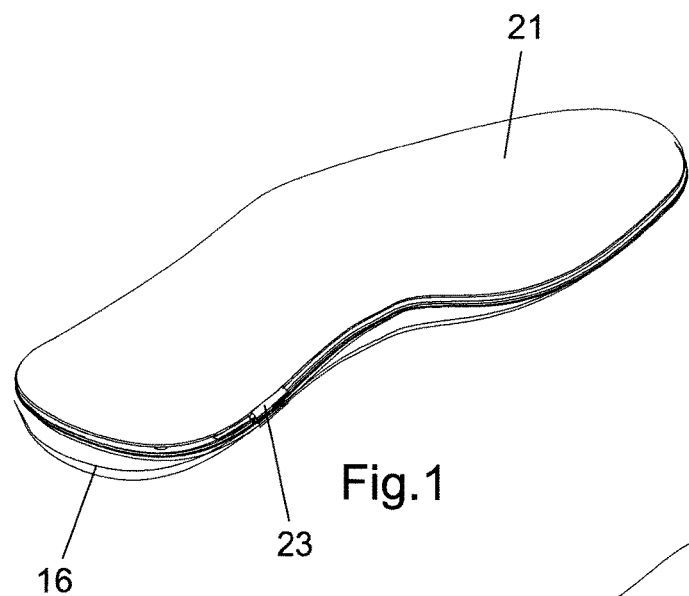
FIG. 1 shows an oblique view of an insole in accordance with the invention.

The (partially simplified and schematized) figures illustrate one exemplary embodiment of an insole according to the invention for a shoe. The insole has a sensor device 10, which has a plurality of sensor fields 1-9, each of said sensor fields being able to detect a pressure acting on the respective sensor field 1-9. The sensor device has layers 11-13 that lie one above another in the manner of a sandwich.

The middle layer 12 consists of a piezoresistive material, that is to say the contact resistance through the middle layer 12 (that is to say at a right angle to the plane of the middle layer 12) is dependent on the pressure load distribution of the middle layer 12. This piezoresistive material can be a piezoresistive nonwoven, for example. A piezoresistive material of this kind can be designed, for example, in the form of a polyester nonwoven, which is coated with an electrically conductive material, in particular a metal or carbon. Piezoresistive materials of this kind are known.

The bottom and top layer 11, 13 each comprise an electrically conductive material 14 in the region 1a-9a; 1b-9b of a respective sensor field 1-9. In the exemplary embodiment, said electrically conductive material 14 is formed by an electrically conductive yarn, with which the base material of the bottom and top layer 11, 13, respectively, is embroidered. A grid-like structure is formed in each case in the respective region 1a-9a; 1b-9b by the embroidered-on conductive yarn. A respective region 1a-9a; 1b-9b could also be embroidered with the electrically conductive yarn at least substantially over the entire surface.

Figure 6:
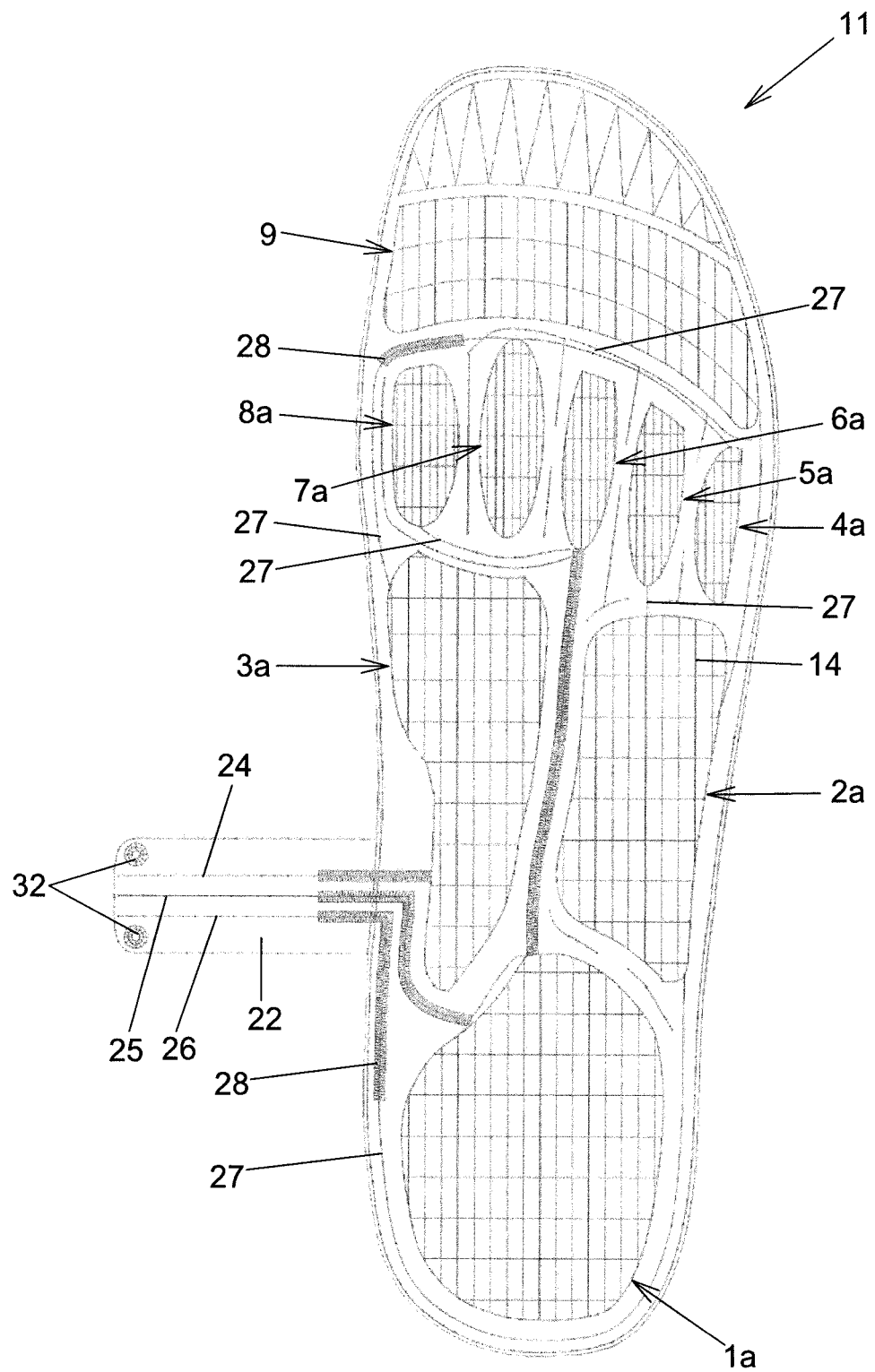
FIG. 6 shows a plan view of the bottom layer of the sensor device.
Figure 7:
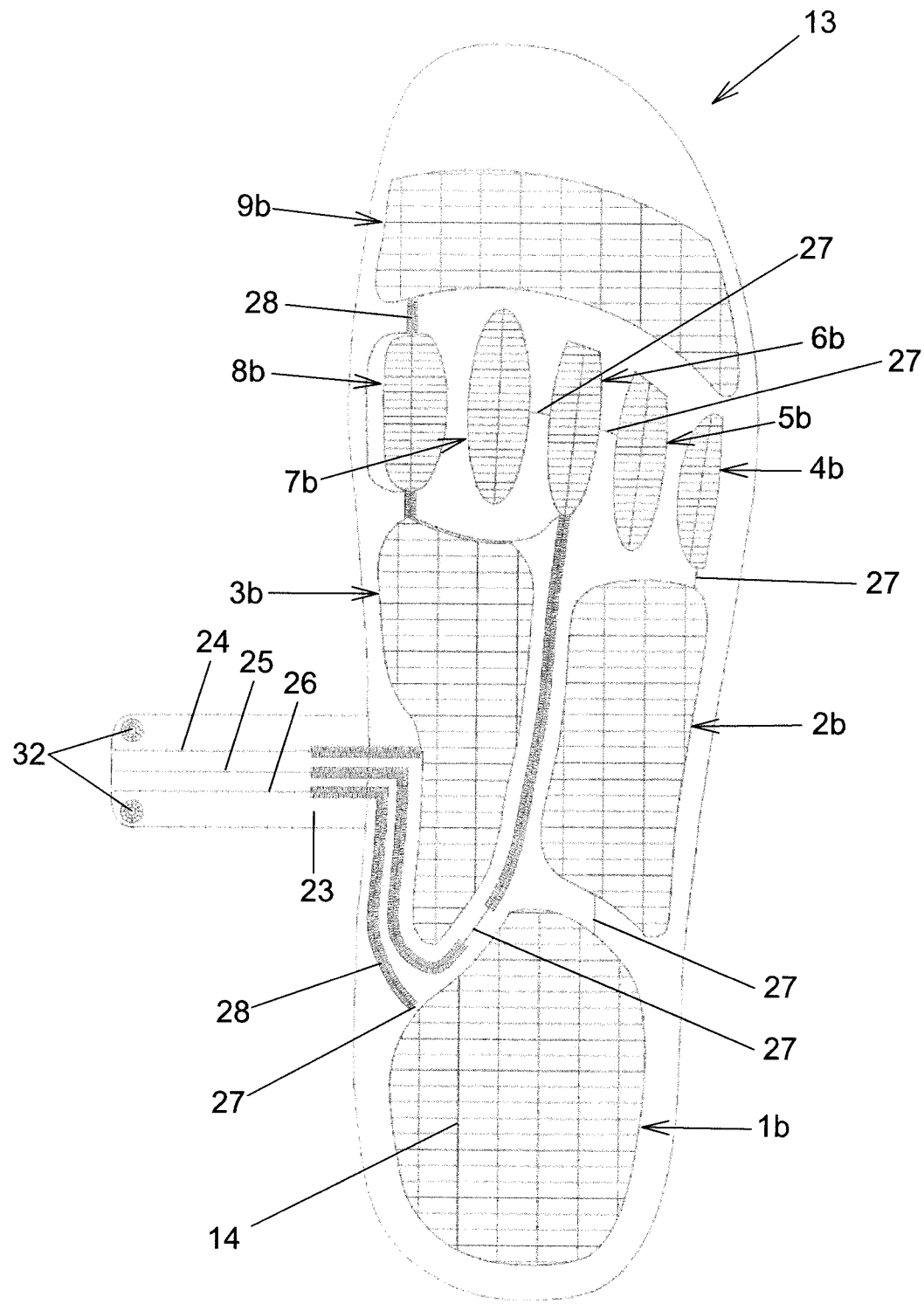
FIG. 7 shows a plan view of the top layer of the sensor device (illustrated with the base material being transparent)
Figure 8:
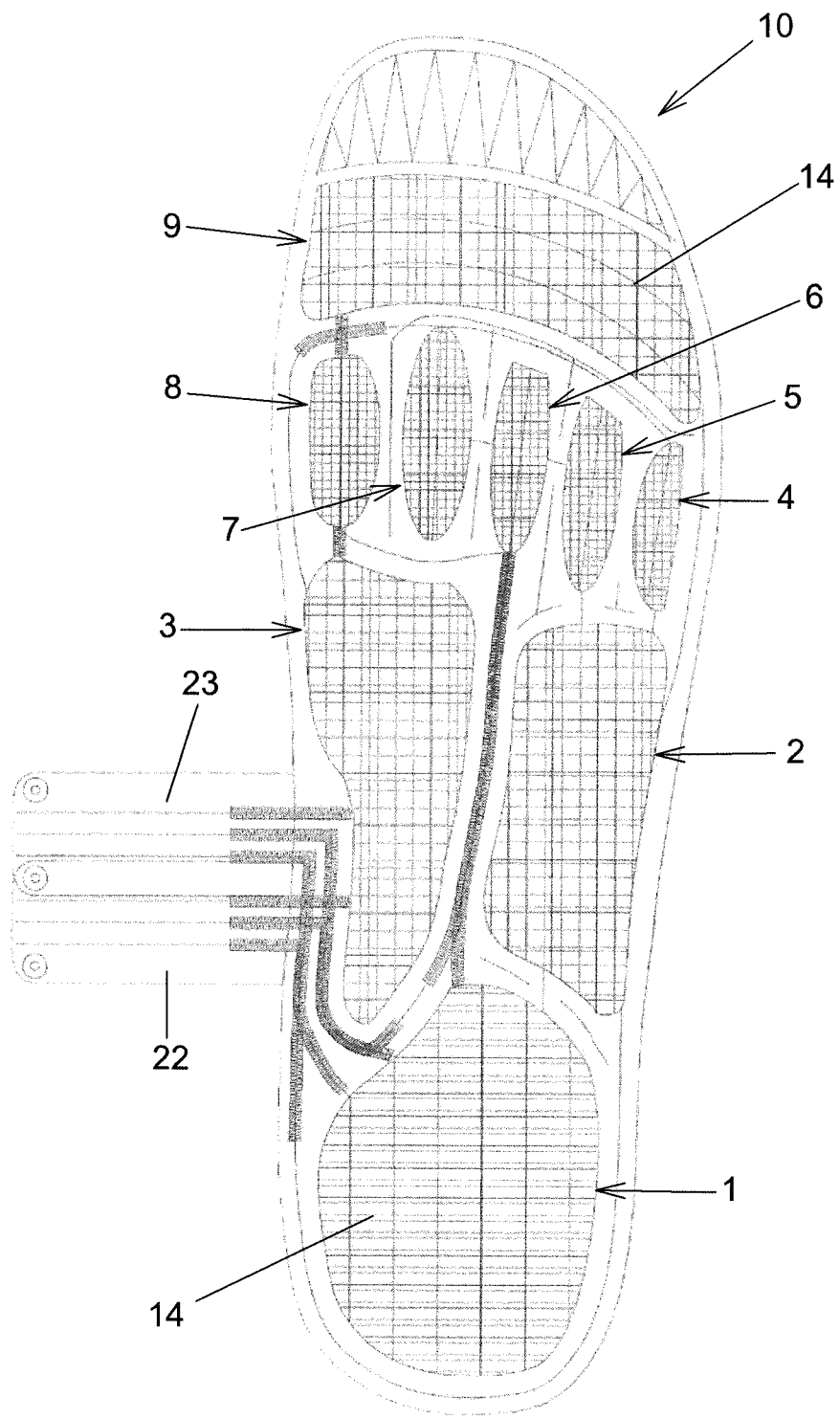
FIG. 8 shows a plan view of the sensor device (illustrated with the base material of the top layer and the middle layer being transparent).

The electrically conductive material 14 is therefore arranged on the top side of the bottom layer 11 (FIG. 6) as well as on the bottom side of the top layer 13 (for this purpose FIG. 7 illustrates the base material of the top layer 13 as transparent in order for the electrically conductive material 14 to be visible).

Figure 2:
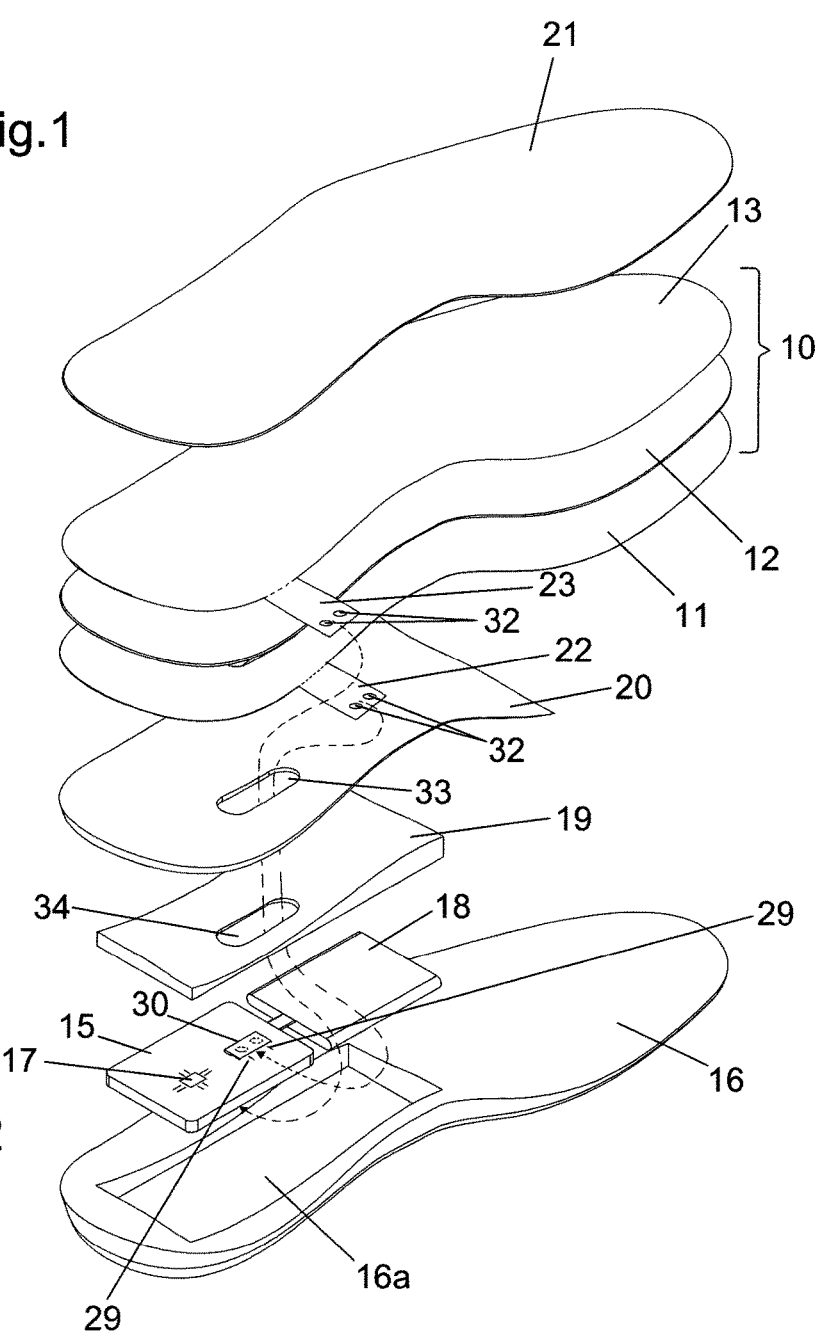
FIG. 2 shows a schematic exploded illustration.

FIG. 2 illustrates only the base material from the bottom layer 11 and top layer 13, but not the conductive material 14, for the sake of simplicity.

The base material is preferably a textile material; for example, the base material can be formed by a polyester fabric.

A respective sensor field 1-9 therefore comprises the respective region 1a-9a of the bottom layer 11, the region 1b-9b of the top layer 13 lying above and the section of the middle layer 12 lying in between. The regions 1a-9a; 1b-9b associated with a respective sensor field 1-9 thus lie one above another and are preferably at least essentially identical in terms of coverage as viewed in a plan view.

The sensor device 10 is electrically conductively connected to an electronic unit 15. The electronic unit 15 is arranged in a recess 16a of a sole base part 16. The electronic unit 15 has electronic components 17, only one of which is illustrated in FIG. 2. In particular, the electronic unit 15 is a printed circuit board, which is populated with the electronic components 17.

A rechargeable battery 18 serves to supply power to the electronic unit 15. This rechargeable battery is likewise arranged in the recess 16a of the sole base part 16 and electrically connected to the electronic unit 15.

The sole base part 16 can be formed of cork, for example.

Further layers, in particular shock-absorbing and/or insulation layers, can be arranged between the sole base part 16 and the sensor device 10. In the exemplary embodiment, a shock-absorbing layer 19, for example made of plastic, is arranged on the sole base part in the region of the recess 16a for absorbing shocks.

In the exemplary embodiment, a stabilizing layer 20 is arranged—advantageously above the shock-absorbing layer 19, if one is provided—between the sole base part 16 and the sensor device 10, said stabilizing layer extending at least over a rear part of the sole base part 16. Said advantageously provided stabilizing layer 20 prevents the sole base part 16 from bending too much in the region of the electronic unit 15 and/or the rechargeable battery 18. The stabilizing layer 20 can consist of plastic.

As illustrated, a layer 21 for supporting the foot can be provided above the sensor device 10, for example made of a textile material.

The various layers 16, 19, 20, 11, 12, 13, 24 of the insole are connected to one another, in particular by adhesive bonding and/or sewing.

The bottom layer 11 and the top layer 13 each have a protruding flexible tab 22, 23 for electrically connecting the sensor fields 1-9 to the electronic unit 15. A respective tab 22, 23 is provided with conductor tracks 24, 25, 26. The conductor tracks 24-26 running over the tabs 22, 23 extend over the bottom layer 11 and top layer 13 and form sensor supply lines 27, in order to connect the electrically conductive material 14 of the relevant regions 1a-9a; 1b-9b to the conductor tracks 24, 25, 26 of the tabs 22, 23.

In the exemplary embodiment, nine sensor fields 1-9 are provided and hence nine regions 1a-9a; 1b-9b, which comprise electrically conductive material 14, of the bottom layer 11 and of the top layer 13, and the tab 22 of the bottom layer 11 and the tab 23 of the top layer 13 both have three conductor tracks 24-26. In this case, the following connections exist in particular:

The conductor track 24 of the tab 22 of the bottom layer 11 is connected to the electrically conductive material 14 in the regions 3a, 7a, 4a, the conductor track 25 of the tab 22 is connected to the electrically conductive material 14 in the regions 1a, 6a and 8a and the conductor track 26 of the tab 22 is connected to the electrically conductive material 14 of the regions 2a, 5a and 9a. The conductor track 24 of the tab 23 of the top layer 13 is connected to the electrically conductive material 14 in the regions 3b, 8b, 9b, the conductor track 25 of the tab 23 is connected to the electrically conductive material 14 in the regions 5b, 6b and 7b and the conductor track 26 of the tab 23 is connected to the electrically conductive material 14 in the regions 1b, 2b and 4b.

The electrical resistance of precisely one of the sensor fields 1-9 can therefore be measured in each case between one of the conductor tracks 24-26 of the tab 22 of the bottom layer and one of the conductor tracks 24-26 of the tab 23 of the top layer 13, for example the electrical resistance of the sensor field 3 can be measured between the conductor track 24 of the tab 22 and the conductor track 24 of the tab 23.

In the exemplary embodiment shown, the conductor tracks 24-26 of the bottom and top tab 22, 23 and the sensor supply lines 27 of the bottom layer 11 and top layer 13 are formed by an electrically conductive yarn, with which the base material of the respective tab 22, 23 and the respective layer 11, 13, respectively, is embroidered.

The sensor supply lines 27 are electrically isolated in the region of intersection points between sensor supply lines 27 of the bottom and top layer 11, 13. In the exemplary embodiment shown, the electrically conductive yarn is over-embroidered with an electrically isolating yarn 28, for example a polyester yarn, in the region to be isolated for this purpose.

The tabs 22, 23 are preferably formed in a materially integral manner with the base material of the respective layer 11, 13. Although the schematized FIG. 5 illustrates the tabs 22, 23 with a smaller material thickness than the respective layer 11, 13, the tabs 22, 23 could have the same material thickness as the respective layer 11, 13, as this is preferred.

To form the bottom layer 11 and the top layer 13, respectively, with the tab 22, 23 respectively arranged thereon, it is therefore possible for a flat, in particular textile, base material to be embroidered with electrically conductive yarn, in order to form the regions 1*a*-9*a*; 1*b*-9*b*, the conductor tracks 24-26 of the tabs 22, 23 and the sensor supply lines 27. As already mentioned, isolations that are to be formed can be produced by embroidering with an electrically isolating yarn. Consequently, the respective layer 11, 13 with the tab 22, 23 arranged thereon can be cut to size. The bottom layer and the top layer can be formed overall in this way by textile production methods.

In the state in which the respective layer 11, 13 with the tab 22, 23 arranged thereon is laid flat, the tab 22, 23 protrudes laterally from the layer 11, 13 and lies in the same plane as the latter. The tabs 22, 23 could also be referred to as lugs.

To form the sensor device 10, the bottom layer 11, the middle layer 12 and the top layer 13 are placed one above the other and connected to one another, for example by sewing.

The electrically conductive yarn for forming the regions 1*a*-9*a*; 1*b*-9*b* of the bottom layer 11 and top layer 13 and/or the conductor tracks 24, 26 of the tabs 22, 23 and/or the sensor supply lines 27 can be a multifilament yarn or a monofilament yarn. For example, said yarn can be a stainless steel yarn, which has several 100 filaments, for example having a thickness in the region of 5 μm to 15 μm. The electrically conductive yarn can also be formed by staple fibers.

To embroider the respective layer 11, 13 and/or tab 22, 23 with the electrically conductive yarn, said electrically conductive yarn can form the back threads, wherein the front threads can be formed by an electrically isolating yarn, for example polyester, or vice versa.

In order to electrically connect the sensor device 10 to the electronic unit 15, the tabs 22, 23 are turned (bent over or folded over about an axis lying parallel to the center plane through the respective layer 11 and parallel to the longitudinal extent of the sole) and placed on contact regions 29 of the electronic unit 15. Only FIG. 1 schematically indicates two such contact regions 29 on the top side of the electronic unit 15. The contact regions 29 are, in particular, metalized regions of the printed circuit board of the electronic unit 15.

In the exemplary embodiment, clamping elements 30 serve to press the conductor tracks 24-26 of the tabs 22, 23 onto the contact regions 29 of the electronic unit 15. A respective clamping element 30 is formed by a resiliently elastic tongue fitted to the electronic unit 15. The clamping elements 30 in this case advantageously have positioning pins 31, which protrude through holes 32 in the tabs 22, 23.

In the exemplary embodiment, the contact regions 29 for the conductor tracks 24-26 of the tab 22 of the bottom layer 11 are located on the top side of the electronic unit 15 and the contact regions 29 for the conductor tracks 24-26 of the tab 23 of the top layer 13 are located on the bottom side of the electronic unit 15. In the case of conductor tracks 24-26 of the two tabs 22, 23 that are not arranged one above another in the plan view, the contact regions 29 for the two conductor tracks could also be arranged on the top side of the electronic unit or the contact regions for the two tabs could also be arranged on the bottom side of the electronic unit.

In the exemplary embodiment, the stabilizing layer 20 and the shock-absorbing layer 19 have window openings 33, 34, through which the tabs 22, 23 are guided in the state in which the electronic unit 15 is connected. It would also be conceivable and possible instead to guide the tabs 22, 23 around the outside of said layers 19, 20.

In the exemplary embodiment, in the state in which the sensor device 10 is laid flat (that is to say in the state in which the electronic unit 15 is not yet connected), the flexible tabs 22, 23 protrude laterally from the sensor device 10, at least substantially in a direction at a right angle to the direction of the longitudinal extent of the insole. Instead, the tabs 22, 23 could also protrude, for example, from the front or rear end of the sensor device 10 (parallel to the direction of the longitudinal extent of the insole), although this is less preferred in view of the risk of damage to the tabs 22, 23.

In order to transmit data of the electronic unit 15, for example to a mobile radio device or another microprocessor device arranged outside of the insole, the electronic unit 15 can preferably have a transmission and reception unit for wireless data transmission, for example via Bluetooth. In one possible embodiment, the rechargeable battery 18 can likewise be charged wirelessly. Instead or in addition, a connection socket (not illustrated in the figures) for data transmission and/or for charging the rechargeable battery 18 could also be provided.

It is possible to use a device according to the invention to detect, inter alia, the pressure acting in each case on the various sensor fields and the time profile thereof, for example in order to determine incorrect load distribution of the user.

The regions 1*a*-9*a*; 1*b*-9*b* with the electrically conductive material 14 could also be formed in a different way to embroidering with an electrically conductive yarn. For example, the bottom and/or top layer 11, 13 could also be provided with a metal coating in these regions.

The conductor tracks 24-26 and/or sensor supply lines 27 could also be formed in a different way to embroidering with a conductive material, for example by metal coatings.

The bottom and/or top layer 11, 13 could also have a film as base material instead of a textile material (said film being embroidered with electrically conductive material and/or being provided with metal coatings).

Isolations could also be formed in a different way instead of over-embroidering with an electrically isolating yarn 28, for example by coating with an electrically isolating material.

The exemplary embodiment shown concerns an insole for a shoe. The invention can likewise be used in a shoe sole of a shoe, said shoe sole being able to be formed in an analogous manner to the insole illustrated, where appropriate with a correspondingly altered layer construction, for example an additional undersole.

| List of Reference Designations | |
|---|---|
| 1 | Sensor field |
| 1a | Region |
| 1b | Region |
| 2 | Sensor field |
| 2a | Region |
| 2b | Region |
| 3 | Sensor field |
| 3a | Region |
| 3b | Region |
| 4 | Sensor field |
| 4a | Region |
| 4b | Region |
| 5 | Sensor field |
| 5a | Region |
| 5b | Region |
| 6 | Sensor field |
| 6a | Region |
| 6b | Region |
| 7 | Sensor field |
| 7a | Region |
| 7b | Region |
| 8 | Sensor field |
| 8a | Region |
| 8b | Region |
| 9 | Sensor field |
| 9a | Region |
| 9b | Region |
| 10 | Sensor device |
| 11 | Bottom layer |
| 12 | Middle layer |
| 13 | Top layer |
| 14 | Electrically conductive material |
| 15 | Electronic unit |
| 16 | Sole base part |
| 16a | Recess |
| 17 | Electronic component |
| 18 | Rechargeable battery |
| 19 | Shock-absorbing layer |
| 20 | Stabilizing layer |
| 21 | Layer |
| 22 | Tab |
| 23 | Tab |
| 24 | Conductor track |
| 25 | Conductor track |
| 26 | Conductor track |
| 27 | Sensor supply line |
| 28 | Electrically isolating yarn |
| 29 | Contact region |
| 30 | Clamping element |
| 31 | Positioning pin |
| 32 | Hole |
| 33 | Window opening |
| 34 | Window opening |

The invention claimed is:

1. An insole or shoe sole, comprising a sensor device having a plurality of sensor fields for pressure detection, an electronic unit that is electrically connected to the sensor fields and has electronic components, the sensor device formed with a sandwich construction including a middle layer made of a piezoresistive material, a top layer arranged above the middle layer and a bottom layer arranged underneath the middle layer, the top and bottom layers each comprising an electrically conductive material forming discrete electrically conductive sections in regions of the sensor fields, wherein between the electrically conductive sections of the top layer as well as between the electrically conductive sections of the bottom layer there are electrically isolating sections, and the top layer having a first protruding tab and the bottom layer having a second protruding tab which is separate from the first protruding tab, the each of the first and second protruding tabs protruding from a margin of the top or bottom layer, respectively, the first protruding tab having conductor tracks connected to the electrically conductive sections of the top layer and the second protruding tab having conductor tracks connected to the electrically conductive sections of the bottom layer, the electronic unit having contact regions which are formed by metalized regions of a printed circuit board of the electronic unit, wherein the first and second protruding tabs are pressed against the contact regions, and wherein the conductor tracks of the tabs contact said contact regions.

2. The insole or shoe sole according to claim 1, wherein the contact regions for the conductor tracks of the tab of the bottom layer are arranged on a top side of the electronic unit and the contact regions for the conductor tracks of the tab of the top layer are arranged on a bottom side of the electronic unit.

3. The insole or shoe sole according to claim 1, wherein the printed circuit board is populated with the electronic components.

4. The insole or shoe sole according to claim 1, wherein the conductor tracks on the tabs are pressed onto the contact regions of the electronic unit by clamping elements.

5. The insole or shoe sole according to claim 1, wherein the electronic unit includes a positioning pin, and a respective one of the tabs has at least one hole, through which the positioning pin protrudes in a state in which the electronic unit is connected.

6. The insole or shoe sole according to claim 1, further comprising at least one of a stabilizing layer or a shock-absorbing layer arranged between the sensor device and the electronic unit.

7. The insole or shoe sole according to claim 6, wherein in the state in which the electronic unit is connected, the tabs extend through a window opening in the at least one of the stabilizing layer or the shock-absorbing layer.

8. The insole or shoe sole according to claim 1, wherein the top layer and the bottom layer each comprise a flexible base material and the tab of the top layer is formed in an integral manner with the base material of the top layer and the tab of the bottom layer is formed in an integral manner with the base material of the bottom layer.

9. The insole or shoe sole according to claim 1, wherein the electrically conductive material of the top layer and the bottom layer in the region of a respective one of the sensor fields, is formed by an electrically conductive yarn that is embroidered with a base material of the top layer and the bottom layer.

10. The insole or shoe sole according to claim 1, wherein the conductor tracks of the tabs are formed by an electrically conductive yarn, with which a base material of the respective tab is embroidered.

11. The insole or shoe sole according to claim 1, wherein the top layer and the bottom layer each comprise a base layer which is electrically isolating and an electrically contacting material which extends over several distinct regions and forming the discrete and electrically conductive sections, each of which form a sensor for pressure detection in said several distinct regions.

* * * * *